US00PP20759P3

(12) United States Plant Patent
Layt

(10) Patent No.: US PP20,759 P3
(45) Date of Patent: Feb. 16, 2010

(54) *LOMANDRA HYSTRIX* PLANT NAMED 'LHCOM'

(50) Latin Name: *Lomandra hystrix*
Varietal Denomination: LHCOM

(76) Inventor: Todd Anthony Layt, P.O. Box 1011, Richmond, NSW (AU) 2753

( * ) Notice: Subject to any disclaimer, the term of this patent is extended or adjusted under 35 U.S.C. 154(b) by 0 days.

(21) Appl. No.: 12/152,427

(22) Filed: May 14, 2008

(65) Prior Publication Data

US 2008/0222760 P1 Sep. 11, 2008

Related U.S. Application Data

(60) Provisional application No. 60/930,811, filed on May 18, 2007.

(51) Int. Cl.
*A01H 5/00* (2006.01)

(52) U.S. Cl. ..... Plt./373

(58) Field of Classification Search ..... Plt./373
See application file for complete search history.

(56) References Cited

OTHER PUBLICATIONS

Australian Plant Varieties Journal vol. 19 No. 2 Aug. 4, 2006. p. 1.*

* cited by examiner

*Primary Examiner*—Annette H Para

(57) ABSTRACT

'LHCOM' is a distinctive variety of *Lomandra hystrix* which is characterized by the combination of its compact, dense plant growth habit, horizontal basal shoot attitude, short plant height and narrow-medium leaf width.

1 Drawing Sheet

Latin name of the genus and species: The Latin name of the genus and species of the novel variety disclosed herein is *Lomandra hystrix.*

Variety denomination: The inventive variety of *Lomandra* disclosed herein has been given the variety denomination 'LHCOM'.

BACKGROUND OF THE INVENTION

The present invention relates to a new and distinct perennial variety of *Lomandra hystrix,* which has been given the variety denomination of 'LHCOM'. Its market class is that of an ornamental grass-like plant. 'LHCOM' is intended for use in landscaping and as a decorative grass-like plant.

The *Lomandra hystrix* variety 'LHCOM ' was first discovered in 2002 in an Australian nursery in the state of New South Wales during a routine inspection of approximately 5000 seedlings of open pollinated *Lomandra hystrix* (unpatented) production stock. 'LHCOM ' is a seedling selection of these open pollinated *Lomandra hystrix.* Initially 200 plants were selected due to their smaller shoot and leaf sizes. These were grown on and further observed. In 2003 these were reduced to 10 selections based on these same desirable traits. Finally in late 2004 a single plant was identified as having a narrower leaf width combined with a compact, dense growth habit with a shorter plant height than the parent form as well as a more horizontal basal shoot attitude. It was named 'LHCOM'.

'LHCOM' was first propagated asexually by division in the state of New South Wales, Australia and has since been asexually propagated by division and micropropagation. The distinctive characteristics of the inventive 'LHCOM' variety are stable from generation to generation; clones of the variety produced by asexual reproduction maintain the distinguishing characteristics of the original plant.

'LHCOM' has a compact, dense growth habit with a more horizontal basal shoot attitude, a short plant height and leaves that are shorter and narrower than common *Lomandra hystrix* (unpatented in the United States).

An application for plant breeders' rights for variety 'LHCOM' has been lodged with the Australian Plant Breeders' Rights Office, and was accepted on May 30, 2006$^{th}$ under Application No. 2006/088.

SUMMARY OF THE INVENTION

'LHCOM' is a distinctive variety of *Lomandra hystrix* which is characterized by the combination of its compact, dense plant growth habit, horizontal basal shoot attitude, short plant height and narrow-medium leaf width.

BRIEF DESCRIPTION OF THE FIGURES

FIG. 1 shows a 'LHCOM' plant.

BOTANICAL DESCRIPTION OF THE PLANT

The following is a detailed botanical description of a new and distinct variety of a *Lomandra hystrix* ornamental grass-like plant known as 'LHCOM'. Plant observations were made on plants grown in New South Wales, Australia. Unless indicated otherwise, the descriptions disclosed herein are based upon observations made in April 2007 of 18 month old 'LHCOM' plants grown in nursery pots.

Those skilled in the art will appreciate that certain characteristics will vary with older or, conversely, younger plants. 'LHCOM' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition. 'LHCOM' has not flowered to date. 'LHCOM' is undergoing further trialing and comparative testing in Australia and the United States.

'LHCOM' is a perennial *Lomandra hystrix* plant which originated from a seedling selected from a population of open pollinated plants of *Lomandra hystrix*. After its selection, 'LHCOM' was asexually propagated by division at Clarendon, New South Wales, Australia. 'LHCOM' ha a narrow-medium leaf blade width combined with a compact, densely shooted plant growth habit and a short plant height, which is unusual for *Lomandra hystrix* plant which usually have a broader leaf blade and a tall plant height. 'LHCOM' has a horizontal basal shoot attitude which creates a plant shape which is more rounded whereas common *Lomandra hystrix* plants usually have a more upright to vertical basal shoot attitude creating a plant shape more like an inverted cone.

Growth Habit, Dimensions and Color

'LHCOM' is a short-medium, rhizomatous plant forming a dense tussock. Average plant height is 70 cm and average plant spread is 110 cm in a 18 month old plant grown in a 300 mm nursery or field pot in Sydney, New South Wales, Australia. The upper and lower side of the leaf is yellow green (RHS 146A) in color. The leaf blade is generally 11 to 12 mm in width, and 60-65 cm in length. The leaf base is cauline, leaf apex is tridentate and leaf surface glaucosity is weak to absent. The leaf venation pattern is parallel; the color is the same as the rest of the leaf (yellow-green RHS 146A; observed autumn 2007). The leaf is generally a uniform width from base to the tip, margins may shred at the base, with a tridentate apex typical of *Lomandra hystrix*. The basal leaf margin color prior to any shredding consists of brown RHS 200D edged with orange white RHS 159B. A representative 'LHCOM' plant is shown in FIG. 1.

Roots

Similar to other *Lomandra hystrix,* 'LHCOM' has a large root structure. The roots are fibrous and spreading, similar to other *Lomandra hystrix*.

Rhizomes

Short (3 cm to 4 cm); rhizome color with the leaf sheath removed is white (RHS 155C); surface texture of the rhizome is smooth.

Inflorescence

'LHBYF' has a medium inflorescence size with each inflorescence emerging to approximately level with the foliage.

The inflorescence is a panicle with single branching and usually 4 branches per node. Flowers are made and born in whorled clusters around each node. Each branch of the panicle is subtended by a bract of length 5-8 cm near the base of the peduncle and reducing in length to 1-2 cm towards the apex of the inflorescence. Each cluster of flowers is subtended by 4 bracts of length 10-20 mm. Inflorescence height is from 35-55 cm and inflorescence width is form 9-12 cm. The peduncle is flattened in profile and peduncle color is approximately yellow-green RHS 145B.

Flowers

Flowers are male and borne in clusters around inflorescence nodes. Tepal color is a dull yellow corresponding approximately to RHS 22A. Flower length is 3-4 mm usually.

Flower Rachis

The length of the flower rachis (the branch of the panicle) is from 20 mm towards the apex to 55 mm towards the middle and base of the inflorescence (observed summer 2006-2007).

Reproductive Organs of Male Florets

Six stamens, anther size is 0.5 mm to 0.8 mm in length, anther color is yellow (approximately RHS 8B), observed summer 2006-2007.

Seed

Flowers are male; seed is not produced.

Flowering Period

Flowering season is from spring to summer.

Lantingness of Bloom

Approximately 14 days in summer flowering in Sydney, New South Wales, Australia.

Fragrance

Fragrance is typical of the species, and of medium strength.

Comparison of 'LHCOM' with Other Varieties of Lomandra hystrix 'LHCOM' is the first of the species and therefore comparison is made to the common species form which is usually reproduced by seed for the market place.

'LHCOM' has a shorter plant height than the common form of *Lomandra hystrix*. This combined with the dense plant growth habit produces a much more compact looking plant than the common form of *Lomandra hystrix*. 'LHCOM' has a horizontal basal shoot attitude which creates a more rounded tussock whereas common form of *Lomandra hystrix* has more upright basal shoot that produce a more conical shaped tussock. The leaf blade width of 'LHCOM' is narrower than that of the common form of *Lomandra hystrix*.

The combination of its compact, dense plant growth habit, horozontal basal shoot attitude, short plant height and narrow-medium leaf width makes 'LHCOM' an attractive ornamental grass-like plant.

Asexual Reproduction

After its initial discovery, 'LHCOM' was transplanted into a 140 mm pot for further trials and testing. After divisions were made for a second generation, 'LHCOM' was observed to retain plant growth characteristics that were noted in the original 'LHCOM' seedling. 'LHCOM' was then divided into many larger pots for further evaluation and introduction to micropropagation at Tumbi Umbi, NSW, Australia.

Environmental Tolerances

'LHCOM' has shown potential for shade tolerance and further shade tolerance tests are underway. The winter hardiness of 'LHCOM' is at least to zone 8 a in the Southeastern United States, and evaluation of winter hardiness is ongoing. 'LHCOM' has been observed to hold color to −10 degrees Celsius without any noticeable change in appearance of the plant. 'LHCOM' has excellent drought tolerance. After severe wilting, 'LHCOM' has been noted to recover with watering. 'LHCOM' does well in sandy soils, but also tolerates heavy, clay-type soils well.

Disease Resistance

'LHCOM' has good resistance to root rot compared with most other *Lomandra hystrix* and evaluation of disease resistance is ongoing.

That which is claimed is:

1. A new and distinct variety of *Lomandra hystrix* plant named 'LHCOM', substantially as described and illustrated herein.

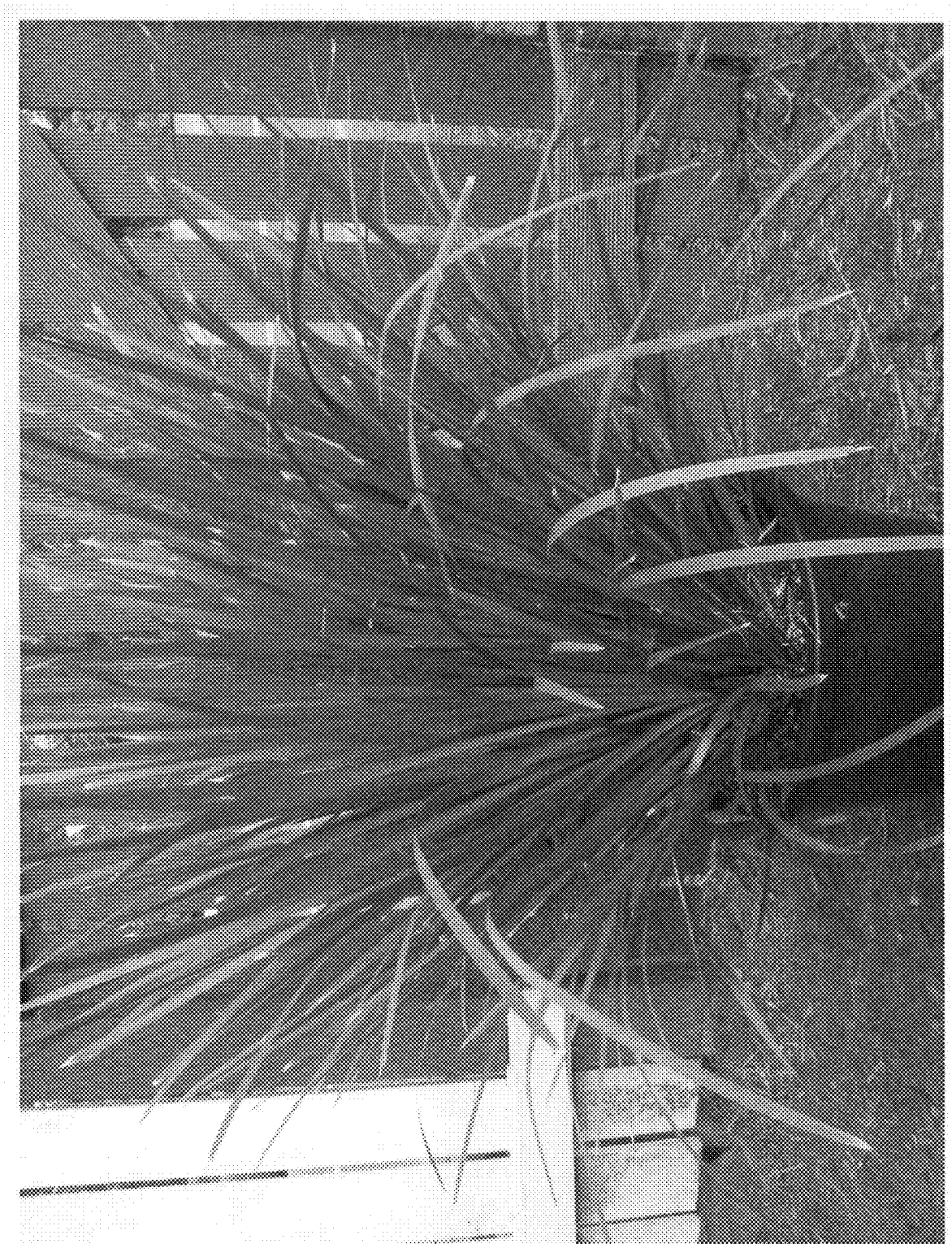

* * * * *